United States Patent [19]
Cheung

[11] Patent Number: 5,448,906
[45] Date of Patent: Sep. 12, 1995

[54] AMBIENT TEMPERATURE GAS SENSOR

[75] Inventor: Jeffrey T. Cheung, Thousand Oaks, Calif.

[73] Assignee: Rockwell International Corporation, Seal Beach, Calif.

[21] Appl. No.: 280,869

[22] Filed: Jul. 26, 1994

[51] Int. Cl.⁶ .................. G01N 27/26; H01C 10/10
[52] U.S. Cl. ...................... 73/31.06; 338/34; 257/253
[58] Field of Search .............. 73/31.06; 338/34, 36; 257/253

[56] References Cited

U.S. PATENT DOCUMENTS

| | | | |
|---|---|---|---|
| 4,001,756 | 1/1977 | Heijne | 338/34 |
| 4,198,851 | 4/1980 | Janata | 73/23 |
| 4,453,151 | 6/1984 | Leary et al. | 338/34 |
| 4,481,499 | 11/1984 | Arima et al. | 338/34 |
| 4,615,772 | 10/1986 | Hetrick | 204/1 T |
| 4,926,156 | 5/1990 | Dickert et al. | 338/36 |

FOREIGN PATENT DOCUMENTS 3519397 12/1986 Germany ............. 73/31.06

OTHER PUBLICATIONS

Melnick, Zinc Oxide Photoconduction, an Oxygen Adsorption Process, Journal of Chemical Physics, vol. 26, p. 1136 (1957).

Primary Examiner—Hezron E. Williams
Assistant Examiner—J. David Wiggins
Attorney, Agent, or Firm—John J. Deinken

[57] ABSTRACT

An ambient temperature solid state sensor for detecting the concentration of a gas includes an insulating substrate, a polycrystalline semiconducting oxide thin film deposited on the substrate such that the gas can be adsorbed on the surface of the film, the film having a low carrier concentration and a high resistivity, a pair of electrodes disposed on the film for measuring the electrical resistance of the film, and a source of light having a wavelength component which is absorbed by the thin film, thereby causing photodesorption of the gas from the surface of the film and establishing the equilibrium between gaseous species in the ambient and gaseous species adsorbed on the oxide surface. The resistance of the thin film is dependent on the amount of adsorbed gas, the measured resistance of the film thereby indicating the concentration of the gas.

10 Claims, 4 Drawing Sheets

AMBIENT TEMPERATURE GAS SENSOR

BACKGROUND OF THE INVENTION

This invention is concerned with a solid state device that senses gases at room temperature.

Traditional gas sensors based on semiconducting oxides must be operated at high temperature to cause thermal desorption of the chemisorbed gas on the surface of the oxide. The thermal desorption allows an equilibrium to be established between the gaseous species in the ambient environment and on the surface of the semiconducting oxide. The amount of adsorbed gas affects the resistance of the oxide; therefore, by monitoring the resistance, the ambient gas concentration can be determined.

The shortcomings of this approach arise out of the requirement for heating the sensor material. The temperature must be high enough to cause a reasonable response rate, i.e., if the temperature is too low, then the thermal desorption will be too slow. Prolonged operation at high temperature, however, can cause irreversible changes in the electrical properties of the oxide, which in turn can cause drift in the measurements.

The heating requirement also leads to problems with size, power and control. The heater controller can require a considerable amount of power and introduces additional expense because of the need to provide a means for maintaining temperature stability.

Electrochemical cells which operate at room temperature are available for measuring gas concentration. These cells, however, tend to exhibit continuous drift of their baseline and need frequent recalibration for this reason. This drift occurs due to a chemical buildup on the reference electrode.

SUMMARY OF THE INVENTION

An ambient temperature solid state sensor for detecting the concentration of a gas includes an insulating substrate, a polycrystalline semiconducting oxide thin film deposited on the substrate such that the gas can be adsorbed on the surface of the film, the film having a low carrier concentration and a high resistivity, a pair of electrodes disposed on the film for measuring the electrical resistance of the film, and a source of light having a wavelength component which is absorbed by the thin film, thereby causing photodesorption of the gas from the surface of the film to establish an equilibrium between the gas in the ambient environment and gas adsorbed on the thin film surface (grain boundary surface). The electrical resistance of the thin film depends on the amount of adsorbed gas. Therefore, the measured resistance of the film indicates the concentration of the gas in the ambient environment.

In another more particular embodiment, the gas may be an oxidizing gas, such as oxygen. In addition, the thin film may be a fine grain polycrystalline semiconducting oxide thin film having a nominal electrical resistance measured between the electrodes to be less than 1 megohms. More specifically, the thin film may be tin oxide or zinc oxide. The thin film may also be doped with an extrinsic impurity to reduce the electron carrier density of the film.

In a specific embodiment, the thin film is zinc oxide and the extrinsic impurity dopant is nitrogen.

The source of light may be supplied by a source of ultraviolet light and/or by a light emitting diode.

DESCRIPTION OF THE INVENTION

Figure 1:
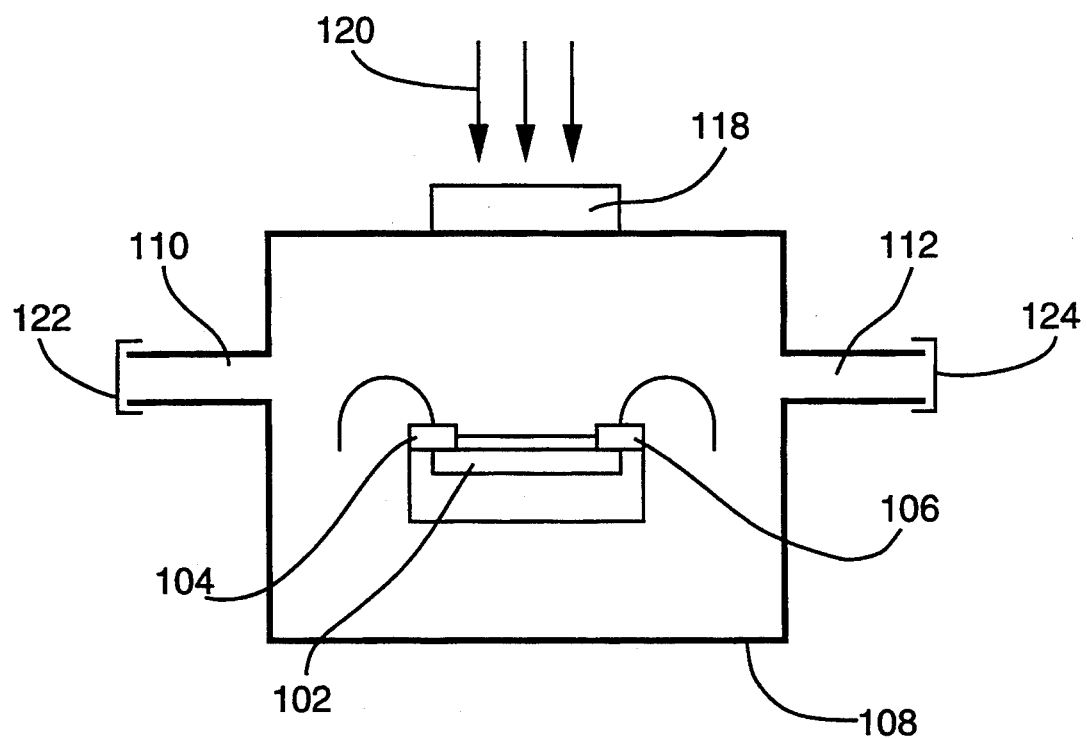
FIG. 1 depicts a solid state gas sensor constructed according to this invention.
Figure 2:
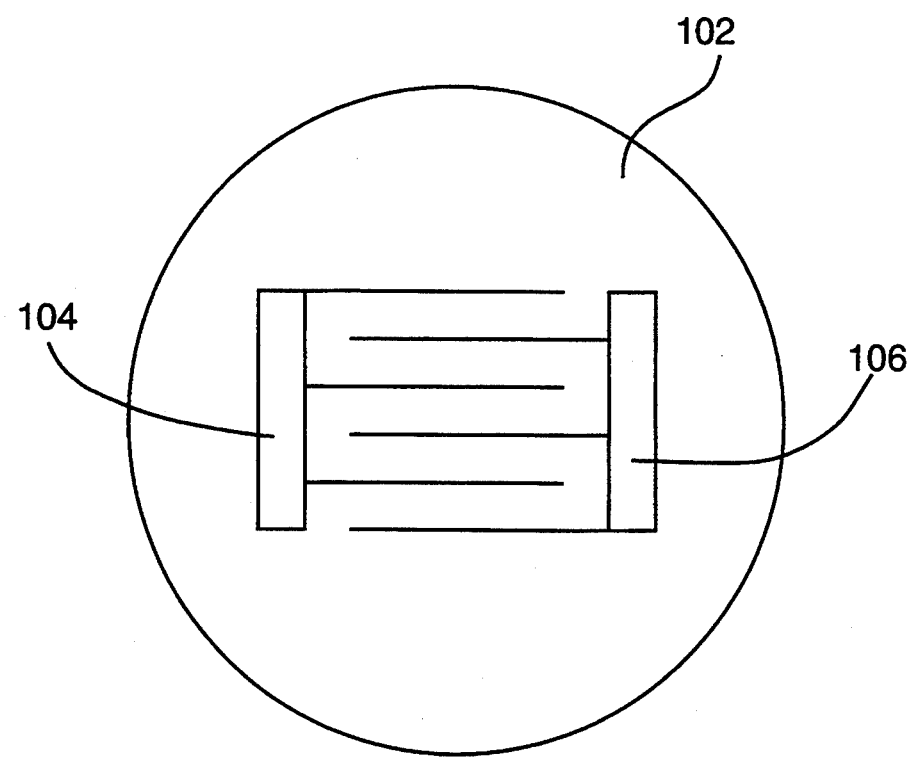
FIG. 2 is a more detailed illustration of the electrode structure for the gas sensor shown in FIG. 1.

FIG. 1 illustrates one embodiment of the solid state gas sensor of this invention. In order to measure the ambient concentration of a gas, a thin film 102 is provided with interdigitated electrodes 104 and 106 (the electrodes are shown in more detail in FIG. 2, which is a plan view of the electrodes and the thin film 102). The film is located within an enclosure 108, which is equipped with an inlet 110, to introduce the gas to be measured into the enclosure, and an outlet 112, to exhaust the gas. A window 118 allows ultraviolet light 120 to be directed onto the surface of the film 102.

In order to detect the concentration of oxygen, for example, the sensor can be exposed to the environment to be monitored or a flow of a gas to be measured is introduced through the inlet 110. The ultraviolet light 120 is absorbed by the film, causing the formation of electron hole pairs in the film. The formation of the electron hole pairs causes photodesorption of the adsorbed oxygen from the surface of the grain boundaries in the film. This desorption enables an equilibrium to be established between the oxygen in the gas and the oxygen on the surface. By then measuring the electrical resistance across the film, using the electrodes 104 and 106, the oxygen concentration in the gas stream can be determined. If the thin film sensor is calibrated, using sources of known concentration, the exact concentration of oxygen can be deduced from the measured resistance of the film.

As those skilled in the art will appreciate, this sensor can also be used to measure the concentration of a gas dissolved in a liquid, such as water, by providing semipermeable membranes 122 and 124 over the inlet 110 and outlet 112, so that the sensor can be immersed in the liquid, allowing only the gas to be measured to enter the enclosure.

Figure 3:
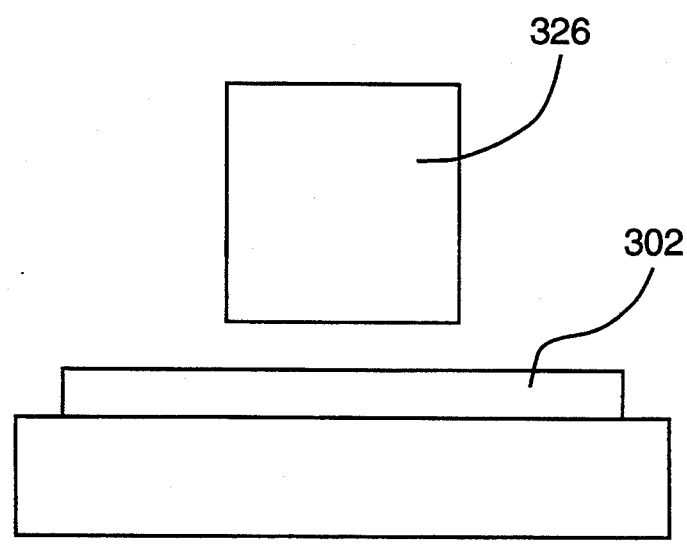
FIG. 3 illustrates a solid state gas sensor constructed according to this invention and using an LED light source.

Alternatively, the sensor can be operated with a light emitting diode (LED) providing the light source. One such embodiment is depicted in FIG. 3, where an LED 326 is positioned very close to the surface of the thin film 302 to provide maximum photon density at the surface of the thin film. The LED 326 is selected to have an output which includes a wavelength component which can be absorbed by the thin film and thereby cause photodesorption of the gas from the surface of the thin film.

Figure 4:
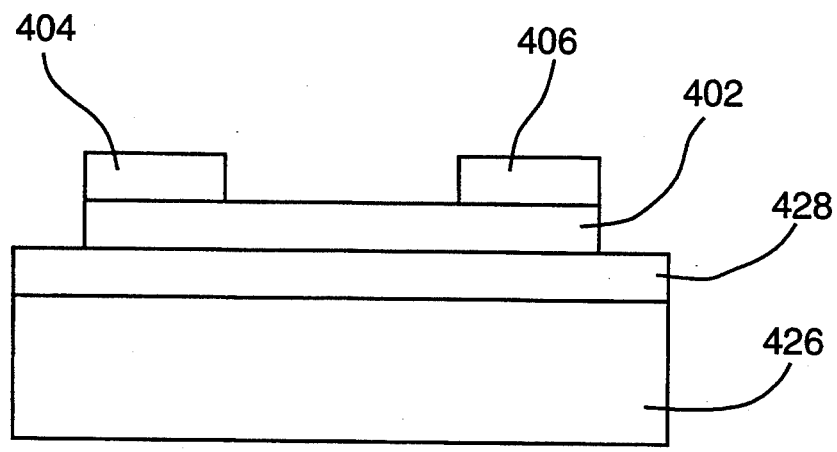
FIG. 4 illustrates an alternative embodiment of a gas sensor utilizing a sensor structure which is integral with the LED light source.

A further improvement to the design of FIG. 3 is shown in FIG. 4, where the thin film sensor is grown directly on the LED structure. Here, a transparent dielectric film 428 is deposited on an LED 426, then the thin film 402 is deposited on the dielectric film 428. The electrodes 404 and 406 are deposited on the thin film 402. The insulating film 428, which can be made of a material such as $SiO_2$, is used to provide electrical insulation. This monolithic architecture simplifies the packaging of the sensor, allows for batch processing, and maximizes the amount of light output from the LED which is used by the sensor.

The sensor of this invention eliminates the need to heat the sensor material. This feature allows the device to be more easily controlled and avoids the irreversible damage which can be inflicted on the bulk properties of a thin film sensor as a result of prolonged heating. The elimination of sensor heating also avoids the need to keep the sensor within a narrow temperature range. Furthermore, the size and the power requirements of the device are reduced.

The preferred embodiments of this invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

I claim:

1. An ambient temperature solid state sensor for detecting the concentration of a gaseous species in an ambient environment, comprising:

an enclosure;

an insulating substrate mounted within the enclosure;

a polycrystalline semiconducting oxide thin film deposited on the substrate such that the gaseous species to be detected can be adsorbed on the surface of the film, the film having a low carrier concentration and a high resistivity;

a pair of electrodes disposed on the film for measuring the electrical resistance of the film; and a source of light, directed toward the film and having a wavelength component which is absorbed by the thin film, thereby causing photodesorption of the adsorbed gaseous species from the surface of the film, establishing an equilibrium between the gaseous species in the environment and the adsorbed gaseous species, and changing the resistance of the film, measured across the electrodes, the measured resistance of the film thereby indicating the concentration of the gaseous species in the ambient environment.

2. The sensor of claim 1, wherein the gaseous species to be detected comprises an oxidizing gas.

3. The sensor of claim 2, wherein the oxidizing gaseous species to be detected further comprises oxygen.

4. The sensor of claim 1, wherein the thin film further comprises a polycrystalline semiconducting oxide thin film having a nominal electrical resistance less than 1 megohms between the pair of electrodes.

5. The sensor of claim 4, wherein the thin film further comprises a fine grain polycrystalline semiconducting oxide thin film.

6. The sensor of claim 5, wherein the thin film is selected from the group consisting of tin oxide and zinc oxide.

7. The sensor of claim 6, wherein the thin film further comprises a thin film doped with an extrinsic impurity to reduce the electron carrier density of the film.

8. The sensor of claim 7, wherein the thin film further comprises zinc oxide and the extrinsic impurity dopant comprises nitrogen.

9. The sensor of claim 1, wherein the source of light further comprises a source of ultraviolet light.

10. The sensor of claim 1, wherein the source of light further comprises a light emitting diode.

* * * * *